United States Patent
David et al.

(10) Patent No.: US 7,983,381 B2
(45) Date of Patent: Jul. 19, 2011

(54) X-RAY CT SYSTEM FOR X-RAY PHASE CONTRAST AND/OR X-RAY DARK FIELD IMAGING

(75) Inventors: Christian David, Lauchringen (DE); Tilman Donath, Brugg (CH); Eckhard Hempel, Fuerth (DE); Martin Hoheisel, Erlangen (DE); Franz Pfeiffer, Brugg (CH); Stefan Popescu, Erlangen (DE)

(73) Assignees: Siemens Aktiengesellschaft, Munich (DE); Paul Scherrer Institut (CH)

( * ) Notice: Subject to any disclaimer, the term of this patent is extended or adjusted under 35 U.S.C. 154(b) by 61 days.

(21) Appl. No.: 12/570,178

(22) Filed: Sep. 30, 2009

(65) Prior Publication Data
US 2010/0091936 A1  Apr. 15, 2010

(30) Foreign Application Priority Data
Sep. 30, 2008  (EP) .................................... 08017240

(51) Int. Cl.
*H05G 1/60* (2006.01)
*G01N 23/04* (2006.01)

(52) U.S. Cl. ............................................. 378/4; 378/62
(58) Field of Classification Search .................. 378/4, 7, 378/19, 62, 63, 84, 150
See application file for complete search history.

(56) References Cited

U.S. PATENT DOCUMENTS

| | | | |
|---|---|---|---|
| 5,812,629 A | 9/1998 | Clauser | |
| 7,180,979 B2 | 2/2007 | Momose | |
| 2007/0153979 A1 | 7/2007 | Baumann et al. | |
| 2007/0183558 A1* | 8/2007 | Hempel | 378/4 |
| 2007/0183584 A1* | 8/2007 | Baumann et al. | 378/145 |
| 2009/0092227 A1 | 4/2009 | David et al. | |
| 2009/0154640 A1 | 6/2009 | Baumann et al. | |
| 2010/0080341 A1* | 4/2010 | Popescu et al. | 378/19 |

FOREIGN PATENT DOCUMENTS
WO   WO 2007/125833   4/2007

OTHER PUBLICATIONS

Hard X-ray Phase Imaging and Tomography with a Grating Interferometer, Weitkamp et al., Developments in X-ray Tomography IV, SPIE vol. 5535, pp. 137-142.
"Tomography With Grating Interferometers at Low-brilliance Sources," Weitkamp et al., Developments in X-ray Tomography V, Paper No. 6318-28.
"Hard-X-ray Dark-Field Imaging Using a Grating Interferometer," Pfeiffer et al., Nature Materials, vol. 7 (2008) pp. 134-137, and Supplementary Information.
"Biomedical Imaging by Talbot-Type X-Ray Phase Tomography," Momose et al., Proc. of SPIE, vol. 6318 (2006) pp. 63180T-1—63180T-10.

* cited by examiner

*Primary Examiner* — Irakli Kiknadze
(74) *Attorney, Agent, or Firm* — Schiff Hardin LLP

(57) ABSTRACT

An x-ray CT system for x-ray phase contrast and/or x-ray dark field imaging has a grating interferometer that has a first grating structure that has a number of band-shaped x-ray emission maxima and minima arranged in parallel, the maxima and minima exhibiting a first grating period, a second band-shaped grating structure that produces, as a phase grating, a partial phase offset of x-ray radiation passing therethrough and that exhibits a second grating period, a third band-shaped grating structure with a third grating period with which relative phase shifts of adjacent x-rays and/or their scatter components are detected, and a device for value-based determination of the phase between adjacent x-rays and/or for value-based determination of the spatial intensity curve per detector element perpendicular to the bands of the grating structures. The third grating structure has a grating period that is larger by a factor of 2 to 5 than the grating period of the first grating structure.

22 Claims, 4 Drawing Sheets

$$I(x) = I_{med} + I_{amp} \cos(x + x_0)$$

X-RAY CT SYSTEM FOR X-RAY PHASE CONTRAST AND/OR X-RAY DARK FIELD IMAGING

BACKGROUND OF THE INVENTION

1. Field of the Invention

The present invention concerns an x-ray CT system (computed tomography) for x-ray phase contrast and/or x-ray dark field imaging of a scanned examination subject.

2. Description of the Prior Art

CT systems for x-ray phase contrast and/or dark field imaging of a subject are known that have at least one grating interferometer arranged at a gantry, the at least one grating interferometer having first, second and third grating structures:

The first grating structure has a number of band-shaped x-ray emission maxima and minima arranged in parallel, the maxima and minima have a first grating period. The second grating structure produces, as a phase grating, a partial phase offset of x-ray radiation passing therethrough and exhibits a second grating period. The third grating structure has a third grating period with which relative phase shifts of adjacent x-rays and/or scatter components are detected. The three grating structures, with regard to their distances from one another and at least the first and second grating structure with regard to their grating periods, satisfy the Talbot conditions.

The known CT systems also have a device for value-based determination of the phase between adjacent x-rays and/or for value-based determination of the spatial intensity curve per detector element perpendicular to the bands of the grating structures.

Such x-ray CT systems for x-ray phase contrast and/or x-ray dark field imaging of a scanned examination subject are known from EP 1 731 099 A1, EP 1 803 398 A1 and DE 10 2006 017 290 A1 for example.

The use of x-ray-optical gratings allows the acquisition of x-ray images in phase contrast, which x-ray images deliver additional information about an examination subject and/or enable a smaller x-ray dose given the same image contrast. The possibility also exists for not only the phase information, but also the amplitude information of scattered radiation, to be used for imaging. An image can be generated that is based exclusively on the scatter components of the x-ray radiation diffracted by the examination subject, thus a least angle scattering. Very slight density differences in the examination subject then can be shown at very high resolution. The publication from F. Pfeiffer et al., "Hard X-ray dark-field imaging using a grating interferometer", Nature Materials 7, pp 134-137 is referenced in this regard.

In order to obtain this desired information of an examination subject irradiated with incoherent radiation from x-ray tubes under practical conditions, three grating structures must be used whose periods lie approximately in the range from 1 to 100 micrometers. The webs of the medium grating structure—the analysis grating—are formed of phase-shifting material and generate a phase shift of $\pi$ or $\pi/2$ according to T. Weitkamp et al.: Proc. SPIE 6318, Developments in X-Ray Tomography V (2006) p. 6318-28. The two other grating structures generally are fashioned as absorption gratings with webs fashioned from absorbing material with the highest possible absorption.

For examinations in which the phase differences between adjacent beams have actually been analytically detected and determined, or in which not only the phase information but also the amplitude information have been analytically determined per pixel at detectors, an arrangement has conventionally been selected in which the distance l between the first and second grating structures $G_0$ and $G_1$ is greater than the distance d between the second and third grating structures $G_1$ and $G_2$. The sample or the gantry opening is arranged between the first and second grating structures $G_0$ and $G_1$. This arrangement results in the corresponding grating periods being $p_0 > p_1 > p_2$. Particularly the technical realization of the grating structure $G_2$ with absorber structures has proven to be problematic since the smallest grating period $p_2$ and the grating lines must have a high absorption. This requires the use of highly absorbent materials such as gold. At the same time, the area of $G_2$ is the largest of all three gratings, which also requires a significant quantity of expensive gold in addition to the production cost.

In FIG. 5 of U.S. Pat. No. 5,812,629, a CT system with a grating interferometer is shown in which the examination subject is arranged between the second and third gratings, wherein the distance between the first two gratings is smaller than the distance between the last two gratings. In this embodiment of the disclosed CT system, however, a value-based analysis of the spatial intensity curve is not implemented per detector element, and thus the phase and amplitude of this intensity curve are also not determined analytically.

In U.S. Pat. No. 7,180,979 B2, an arrangement is disclosed in which the examination subject is positioned between the second and third gratings; but in this embodiment of the CT system a value-based analysis of the spatial intensity curve is not implemented for each detector element, and thus the phase and amplitude of this intensity curve are also not determined analytically.

Furthermore, in published Patent Application WO 2007/12533 A1, a CT system for value-based determination of phase shifts with a Talbot interferometer is proposed in which the grating periods increase in the beam direction, wherein the examination subject can be placed between the second grating structure and third grating structure; however, the ratios of the grating periods relative to one another and the ratios of the intervals between the gratings that are proposed there are unsuitable in practice with a CT system.

SUMMARY OF THE INVENTION

An object of the present invention is to provide an x-ray CT system for x-ray phase contrast and/or x-ray dark field imaging of a scanned examination subject with at least one grating interferometer arranged on a gantry, that poses lower technical requirements for the grating structures that are used within the scope of the Talbot conditions and that is suitable for practical operation for the examination of objects of the size of human patients. This object is achieved by a CT system based on the following insights.

The conditions (=Talbot conditions) of the grating periods $p_0$, $p_1$ and $p_2$ of the grating structures $G_0$, $G_1$ and $G_2$ and the distances l between $G_0$ and $G_1$ and d between $G_1$ and $G_2$ can be described as follows:

$$\frac{p_0}{p_2} = \frac{l}{d} \qquad (1)$$

The grating $G_1$, which is exposed by a spherical wave with the radius l and the wavelength $\lambda$, generates an interference pattern with maximum contrast at a distance TD' due to the Talbot effect, with $$TD' = \frac{1 \cdot TD}{1 - TD} \quad (2)$$

wherein $$TD = \frac{p_1^2}{8\lambda} \quad (3)$$

is the Talbot distance for a plane wave. In order to obtain optimal contrast in the measurement, $G_2$ should be set at the distance TD'; thus d=TD'. At the same time, the grating period $p_2$ should be selected equal to the period of the interference pattern. For this interference pattern, $$p_2 = \frac{p_1}{2} \cdot \left(1 + \frac{d}{l}\right) \quad (4)$$

For a given total length of the measurement structure s=l+d, an astonishingly simple quadratic equation for l results (with the aid of Equations (2) and (3)) as:

$$l^2 - sl + sTD = 0 \quad (5)$$

with the solutions $$l_{1,2} = \frac{s}{2} \pm \sqrt{\frac{s^2}{4} - sTD} = \frac{s}{2} \pm \sqrt{\frac{s^2}{4} - s\frac{p_1^2}{8\lambda}} \quad (6)$$

For $p_1 > \sqrt{2s\lambda}$, the discriminant is less than zero; there is thus no solution within the total length s for such grating periods of the analysis grating $G_1$. $p_1 > \sqrt{2s\lambda}$ yields a symmetrical structure in which l=s/2=d and $p_0=p_1=p_2$. However, this case leaves no space for a large sample or a large gantry opening in the middle between source and detector. The root term in Equation (6) describes the maximum possible radius r of a gantry opening with:

$$r = \sqrt{\frac{s^2}{4} - s\frac{p_1^2}{8\lambda}} \quad (7)$$

There are two solutions for $p_1 > \sqrt{2s\lambda}$. In the previous prior art, only the case in which l is greater than d and the examination subject is correspondingly positioned between the first and second grating structure has been taken into account in CT systems in which analytical values of the phase between adjacent coherent x-rays have actually been determined per detector element.

Based on these insights, and contrary to previous practice, it has been determined in accordance with the invention to select a design in which l is smaller than d. Due to the Talbot conditions described above, it is achieved that the grating period $p_2$ of the third grating structure $G_2$ is greater than the grating period $p_1$ of the second grating structure $G_1$, and this in turn is greater than the grating period $p_0$ of the first grating structure $G_0$. Since, due to geometry, the surface of the first grating structure $G_0$ is to be smaller than that of the second, and this in turn is smaller than that of the third grating structure, a significantly simpler design of the interferometer results.

However, this aforementioned knowledge alone is not sufficient to already establish (within the scope of the fundamental Talbot conditions that must be complied with) the correct size ratios for the grating periods and the correct spacing of the gratings. Relations are merely defined that are to be maintained in order to obtain a functional system.

The invention is thus based on the further insight that, while complying with these aforementioned conditions, it is particularly advantageous for the CT system to be designed in terms of its dimensioning so that the third grating structure has a grating period that is larger at least by a factor of 2 to 5 than the grating period of the first grating structure. In the embodiment it is furthermore advantageous when the second grating structure has a grating period that is larger by a factor of 1.4 to 2.0 than the grating period of the first grating structure. Furthermore, it is advantageous when the ratio of the distance d between the second grating structure and the third grating structure to the distance l between the first grating structure and the second grating structure lies in the range l/d=2.5 to l/d=6. It is particularly advantageous when the energy of the x-ray spectrum that is used lies in the energy range from approximately 50 keV to 80 keV, advantageously at 60 keV. Accordingly, the grating structures should be matched to an x-ray energy in the energy range from 50 keV to 80 keV, in particular 60 keV.

In comparison to the previously used arrangement, such an arrangement entails the following advantages:

1. The grating with the smallest grating period (which is correspondingly difficult to manufacture) is now $G_0$, which has a much smaller area than $G_2$. This reduces the effort and cost.
2. $G_0$ can be replaced by a correspondingly structured anode or, respectively, a correspondingly structured electron beam on an anode which is possibly simpler to realize than a grating and can more easily be moved in steps or continuously.
3. Although the grating $G_1$ has the same period $p_1$, its dimensions are markedly reduced in comparison to the conventional arrangement (likewise thereby a cost reduction).
4. The grating with the largest area is now (only) the grating $G_2$; the requirements for the mictrostructuring are significantly less due to the large grating period $p_2$.
5. Due to the coarser period, the grating $G_2$ can also be produced from less strongly absorbent material than the previously used gold since the webs can be made thicker in a comparably unproblematic manner. The use of, for example, lead instead of gold can markedly reduce the costs.
6. $p_2$ can be selected so large that it can be omitted and replaced with a band or pixel detector with corresponding period. This simplifies the design and avoids that the half of the x-ray photons available after the sample is absorbed in $G_2$.

The phase sensitivity of the conventional arrangement and the arrangement proposed here is the same according to current findings.

Based on these insights, the invention improves the known x-ray CT system for x phase contrast and/or x-ray dark field imaging or a scanned examination subject with at least one grating interferometer arranged on a gantry, wherein the at least one grating interferometer has a first grating structure with a number of band-shaped x-ray emission maxima and minima arranged in parallel that has a first grating period, a second band-shaped grating structure that produces as a phase grating a partial phase offset of a passing x-ray radiation and that has a second grating period, a third band-shaped grating structure with a third grating period with which a relative phase shift of adjacent x-rays and/or their scatter components are detected, wherein the three grating structures satisfy the Talbot conditions with regard to their separations among one another and at least the first and second grating structure and with regard to their grating periods, and a device for value-based determination of the phase between adjacent x-rays and/or for value-based determination of the spatial intensity curve per detector element perpendicular to the bands of the grating structures.

The improvement according to the invention is that the third grating structure has a grating period that is greater by at least a factor of 2 to 5 than the grating period of the first grating structure.

It is advantageous for the second grating structure to have a grating period that is greater by a factor of 1.4 to 2.0 than the grating period of the first grating structure.

Furthermore, it is advantageous for the ratio of the distance d between the second grating structure and the third grating structure to the distance l between the first grating structure and the second grating structure to be in the range of l/d=2.5 to l/d=6.

Furthermore, it is advantageous for the examination of larger subjects for the at least one grating interferometer to have a beam path that, in the direction of a rotation angle of the gantry, exhibits a divergence of at least 30°, advantageously of at least 35° to 40°.

The examination subject can advantageously be positioned between the second grating structure and the third grating structure; a relatively large and central measurement field can hereby result.

In the x-ray CT system according to the invention, a dimension of the first grating structure in the circumferential direction of the gantry can also be selected that is 1 to 3 cm, advantageously approximately 2 cm.

Furthermore, the dimension of the third grating structure in the direction of the greatest divergence of the radiation that is used can be greater by at least a factor of two than the dimension of the second grating structure in the direction of the greatest divergence of the radiation used.

With regard to the ratio l/d of the distance l between the first and second grating structure and the distance d between the second and third grating structure, it is proposed that this is smaller than 1, advantageously is between the values l/d=0.4 and 0.2. The design of a grating interferometer for a CT system is therefore possible that enables a sufficiently large measurement field which is located in the rotation center of a gantry when the interferometer is installed.

In a conventional embodiment, the first grating structure can possess a source grating with focus of an x-ray source situated upstream in the beam direction. Known designs of x-ray tubes can therefore be resorted to, wherein only a relatively small absorption grating as a source grating is to be positioned in the region of the exit window.

As an alternative to the use of a source grating, the first grating structure can also be formed by radiation maxima and radiation minima alternately escaping in bands at an anode.

Different methods are known to form such band-shaped radiation maxima and radiation minima of x-ray radiation. For example, an anode can be used that possesses an inhomogeneously structured anode surface, whereby the radiation maxima and radiation minima escaping in alternation are created. Such an inhomogeneity can be formed in that the anode surface possesses elevations and/or depressions arranged in bands. However, the possibility also exists to arrange band-shaped materials with different atomic number on the anode surface. A combination of the two last cited possibilities is also possible in that different materials are present at the surface in the depressions than at relative elevations. A suitable design is shown in EP 1 803 398 A1.

An additional possibility to generate band-shaped radiation maxima and minima on a surface is to provide a deflection device of an electron beam operating on an electromagnetic basis, which deflection device scans the anode surface with the electron beam and therefore generates the band-shaped radiation maxima and radiation minima escaping in alternation. This variant of the design is shown in EP 1 803 398 A1.

For a value-based analysis of a phase between adjacent x-rays, the third grating structure can be designed such that it has at least one analysis grating with subsequently arranged, spatially resolving detector with a plurality of detector elements. Furthermore, a device for monitored spatial offset perpendicular to its grating lines and with a spatial resolution in the range of the period of the first grating structure. Alternately, to move the analysis grating the second grating structure can also possess a device for monitored spatial offset perpendicular to its grating lines, and with a spatial resolution in the range of the period of the second grating structure, or the third grating structure also possesses a device for monitored spatial offset perpendicular to its grating lines and with a spatial resolution in the range of the period of the third grating structure. In principle the possibility also exists to move the subject itself, but this does not appear to be practical, at least given a scan of a patient.

Instead of the movement of grating structures, a third grating structure can also be used that is formed by a number of band-shaped, spatially resolved detector elements per detected x-ray beam as is described in, for example, DE 10 2006 017 290 A1.

DESCRIPTION OF THE PREFERRED EMBODIMENTS

Figure 1:
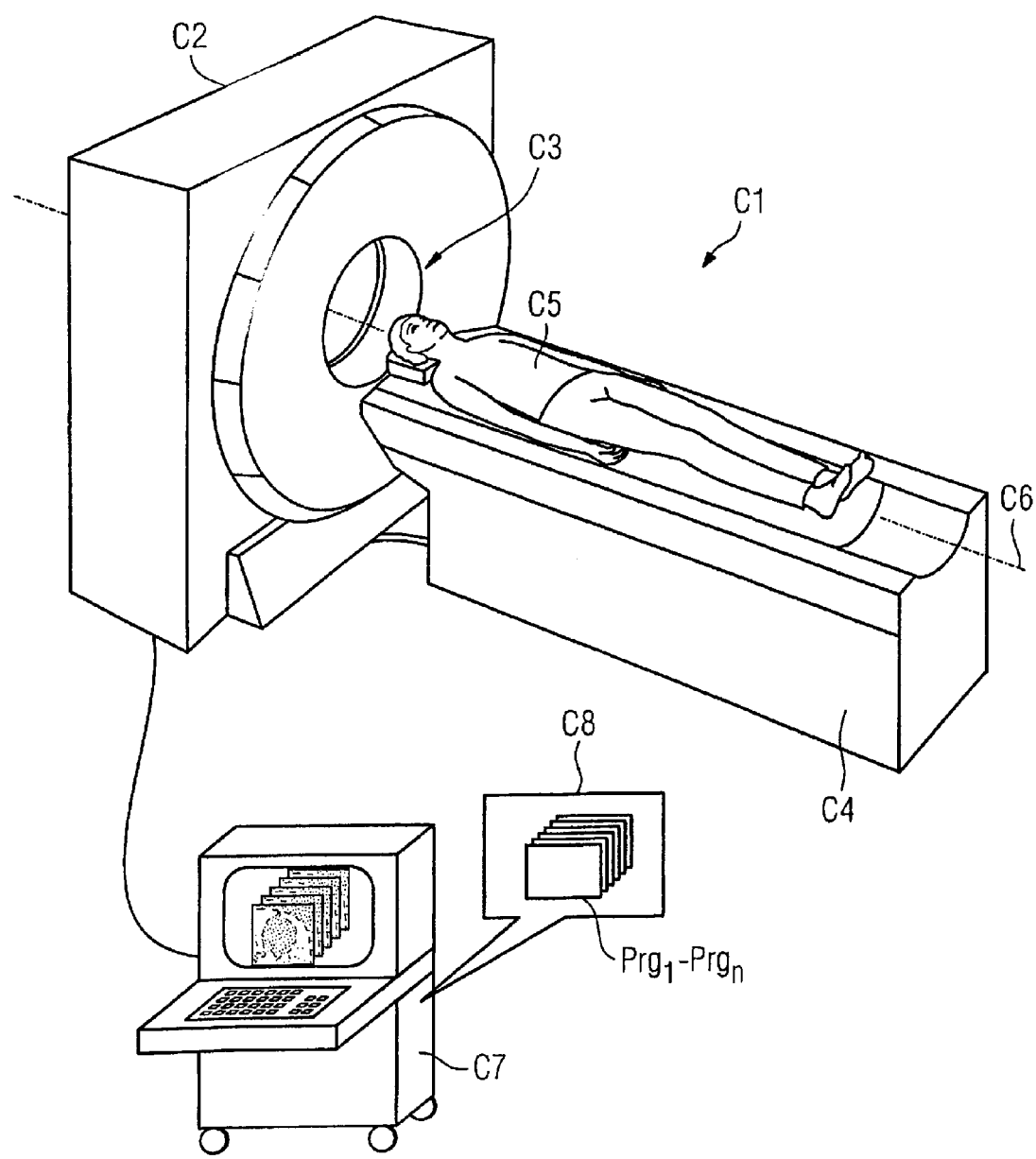
FIG. 1 shows an x-ray CT system with beam detector system according to the invention in 3D representation.

In the following the invention is described in detail with the aid of Figures, wherein only the features necessary for understanding the invention are shown. The following reference characters, variables and abbreviated designations are used: C1: x-ray CT system; C2: gantry housing; C3: gantry opening; C4: displaceable patient bed; C5: patient; C6: system axis; C7: control and computer unit; C8: memory; d: distance between second grating and third grating; D: detector; $E_i$: detector elements; F: focus; $G_0$: source grating; $G_1$: phase grating; $G_2$ analysis grating; l: distance between first grating and second grating; M: measurement field: $p_0$: grating period of the first grating structure; $p_1$: grating period of the second grating structure; $p_2$: grating period of the second grating structure; $Prg_1$-$Prg_n$: computer programs; r: radius; s: distance between first grating and third grating; S: beam cone; $S_1$, $S_2$: adjacent x-ray beams; α: divergence.

An x-ray CT system C1 according to the invention for x-ray phase contrast and/or x-ray dark field imaging of a scanned examination subject with at least one grating interferometer arranged on a gantry is shown in 3D representation in FIG. 1.

The system is essentially composed of a gantry housing C2, a displaceable patient bed C4 and a control and computer unit C7. A gantry opening C3 is shown in the gantry housing C2 the gantry opening C3 corresponding in terms of its diameter to approximately twice the radius 2r of the measurement field of grating interferometer or grating interferometers (not visible here) at the gantry. According to the invention, the grating structures of the grating interferometers used here are arranged relative to the measurement field (and therefore to the gantry opening C3) so that the phase grating is located at the source side and the analysis grating structure is located at the detector side. Corresponding to the geometric Talbot conditions described above, the grating structures are therefore also fashioned with regard their grating periods so that the relative smallest grating structure of the source grating $G_0$ also has the smallest grating period $p_0$ and the largest (in terms of area) grating structure of the analysis grating $G_2$ also has the largest grating period $p_2$, wherein the phase grating $G_1$ is arranged in-between with regard to dimensions and grating period. A CT system is achieved with a justifiable design cost.

For measurement, the patient C5 is sequentially or continuously displaced (moved) through the measurement field with the aid of the displaceable patient bed C4 given a rotating gantry along the system axis C6, wherein a scan is implemented with the one or multiple grating interferometer(s) rotating with the gantry around the system axis C6. Given the scan and the following evaluation of the detector data, the phase differences of adjacent, coherent x-rays are quantitatively determined and/or dark field CT exposures are reconstructed from projections, similar to the known dark field exposures from microscopy. For this purpose, the diffracted radiation components of the scanning x-ray radiation are initially determined from a plurality of projection angles. These projective exposures are subsequently used in order to reconstruct tomographical image data with the aid of known reconstruction techniques that reflect volume-specific least angle scatterings as is shown by, for example, F. Pfeiffer et al., "Hard X-ray dark-field imaging using a grating interferometer", Nature Materials 7, pp 134-137. It is noted that a precise quantitative knowledge of the spatial intensity curve perpendicular to the band direction of the grating structures within every x-ray beam is necessary for these acquisitions.

The computer programs $Prg_1$-$Prg_n$ that are stored in a memory C8 of the control and computer unit C7 and that can be recalled and executed as necessary can hereby serve to implement the control, measurement and reconstruction.

Figure 2:
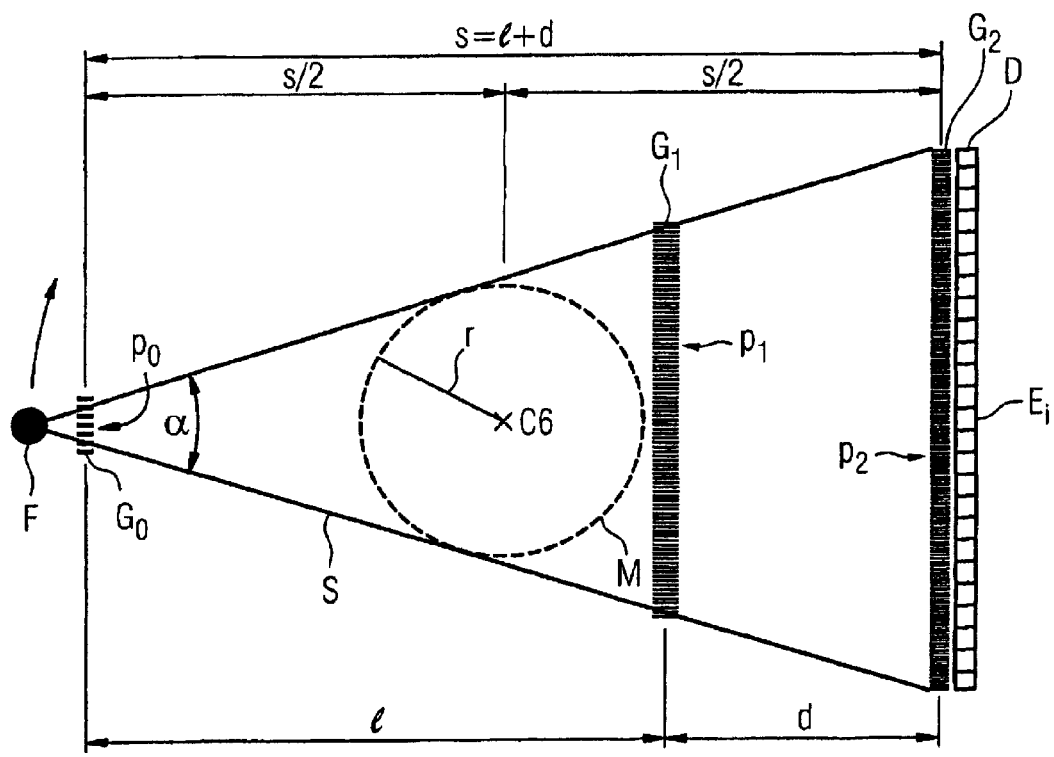
FIG. 2 shows a known beam detector system of a CT designed as a grating interferometer.

FIG. 2 shows the basic design of a grating interferometer in a previously used arrangement with its typical dimensions. A focus F of a radiation source is shown to the left which follows a first absorption grating (which turns out to be relatively coarse with regard to the grating period $p_0$) as a source grating $G_0$. The measurement field M which corresponds approximately to the gantry opening C3 with the radius r is subsequently arranged in the beam cone S that possesses a large divergence α. In a realistic CT system in which the measurement system (and not the examination subject) rotates, the measurement field M is arranged concentric relative to the system axis C6 of the gantry. In the beam direction the phase grating $G_1$ now follows with a smaller period $p_1$, and after this the third grating structure $G_2$ with again a smaller grating period $p_2$. In the shown exemplary embodiment, the grating structure $G_2$ is formed by the analysis grating itself and a subsequent detector D with its detector elements $E_i$.

As is recognizable from the shown example, this arrangement at the detector side requires a very large (in terms of area) but simultaneously very finely structured absorption grating as a third grating structure. Such an embodiment is, however, realized only at great cost given a large divergence α.

In an embodiment according to the invention, therefore, the second grating structure $G_1$ is displaced to the other side of the measurement field M and the grating periods $p_0$, $p_1$ and $p_2$ become greater in the beam direction so that the largest (in terms of area) third grating structure $G_2$ is also the simplest to manufacture.

Figure 3:
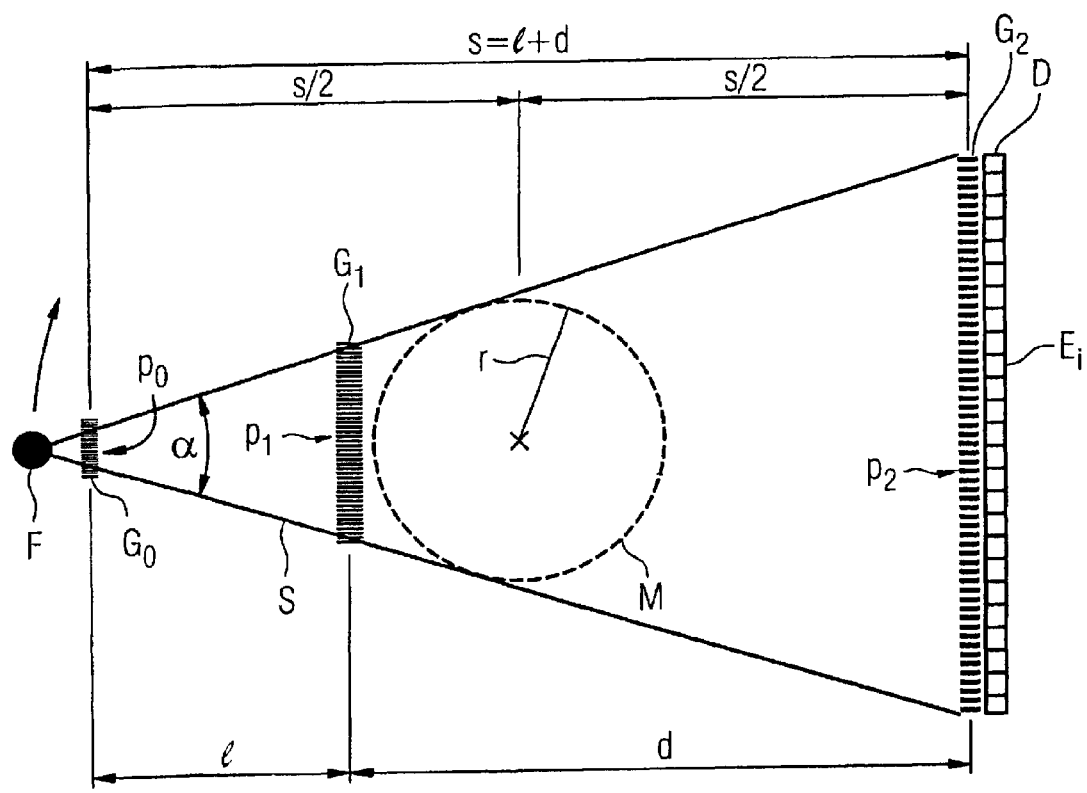
FIG. 3 shows a beam detector system according to the invention.

Such an exemplary design of a grating interferometer is shown in FIG. 3. The characteristic distances s, l and d are—as in FIG. 2—likewise drawn. Typical values are shown in the following Table 1:

TABLE 1

| | s = l + d | 2r | α | l | d | E | $p_0$ | $p_1$ | $p_2$ |
|---|---|---|---|---|---|---|---|---|---|
| CT geometry 1 | 1050 mm | 700 mm | 37° | 175 mm | 875 mm | 60 keV | 2.95 μm | 4.91 μm | 14.7 μm |
| CT geometry 2 | 1050 mm | 500 mm | 27° | 275 mm | 775 mm | 60 keV | 3.92 μm | 5.79 μm | 11.1 μm |
| CT geometry 3 | 1250 mm | 700 mm | 31° | 275 mm | 975 mm | 60 keV | 3.81 μm | 5.95 μm | 13.5 μm |

As proceeds from Table 1, a grating interferometer to be used in a CT system can be dimensioned such that a sufficiently large measurement field with a radius r of 700 mm remains between the second and third grating structure, but a measurement field in the region of the third grating structure is achieved for grating periods of greater than 10 μm that can be generated with a still-justifiable expenditure.

Figure 4:
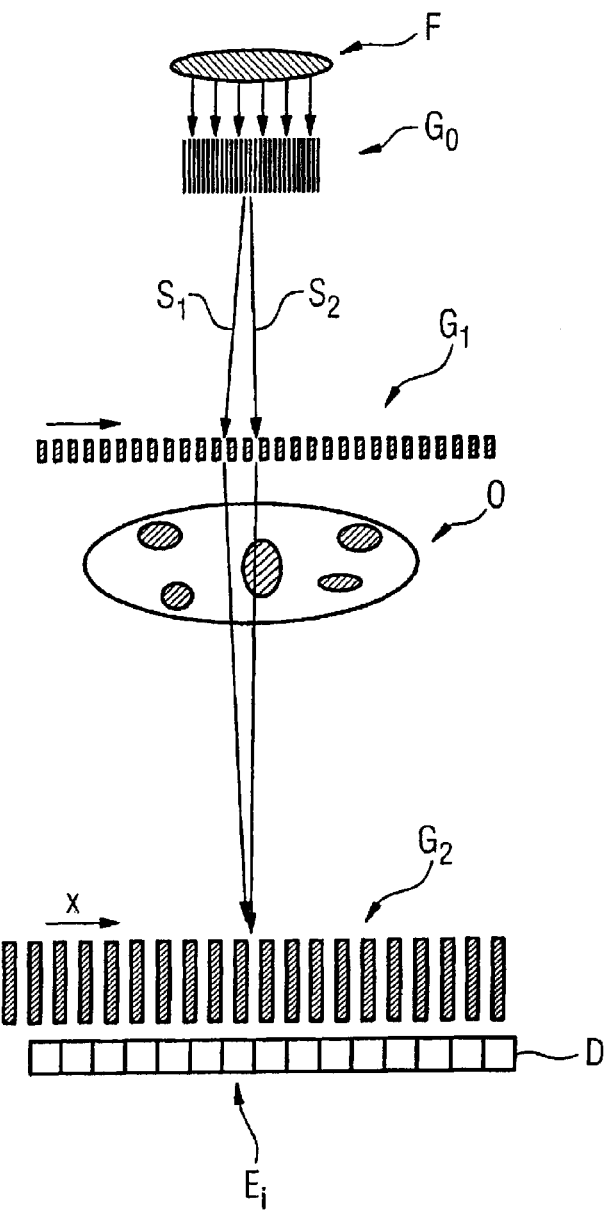
FIG. 4 is a basic representation of the measurement principle for x-ray phase contrast and x-ray dark field measurement.
Figure 4:
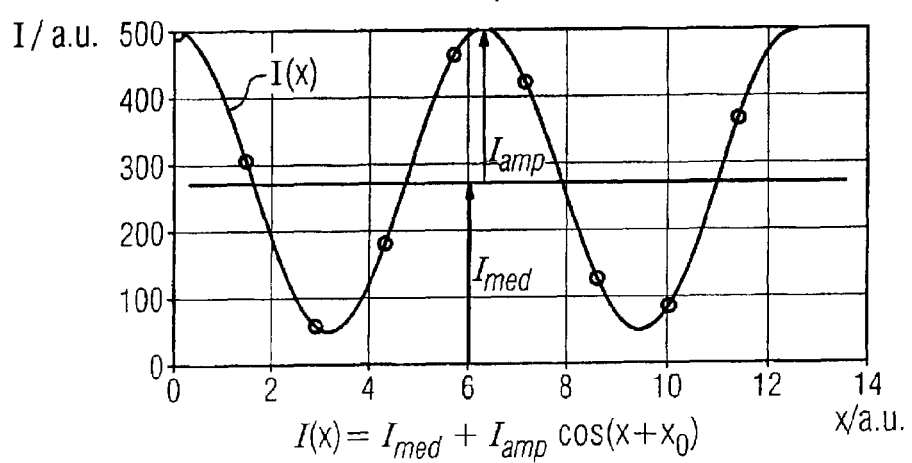

FIG. 4 is referred to for a better understanding of the measurement principle of the CT systems according to the invention with grating interferometers. Shown here are a large-area focus F as an x-ray source and a subsequently arranged source grating $G_0$ that here forms the first grating structure. Band-shaped, quasi-coherent x-rays are hereby radiated at the gaps of the source grating $G_0$ while they are largely suppressed in the range of the absorption of the webs of the grating. Two adjacent, coherent x-ray beams $S_1$ and $S_2$ are respectively shown as examples that strike a phase grating $G_1$ in a beam course, in which phase grating $G_1$ a diffraction of the beams occurs so that, following the phase grating $G_1$, an interference pattern of the diffracted x-ray radiation arises. To show this interference pattern a third grating (the analysis grating) is used which is situated upstream of a detector D with a plurality of detector elements $E_i$. Via the interaction of the periodic interferences of the x-ray radiation with the analysis grating $G_2$, an intensity fluctuation of the passing x-ray radiation results after the analysis grating depending on the position of the analysis grating $G_2$, which fluctuation can be measured at the individual detector elements $E_1$ of the detector depending on the displacement of the grating $G_2$ or, respectively, also on displacements of the other upstream gratings. The subject to be examined is positioned between the phase grating $G_1$ and the subsequent analysis grating $G_2$.

If the effect of the displacement of a grating structure in the x-direction on the intensity measurement of a detector element $E_1$ is considered, an intensity curve l(x) results depending on the grating deflection x as it is shown at the bottom in FIG. 4 in the form of a sinusoidal oscillation. The following applies:

$$l(x)=l_{med}+l_{amp}\cos(x+x_0)$$

The course of this curve can be completely described by the specification with median value $l_{med}$, the specification of the deflection amplitude $l_{amp}$ and the phase $x_0$ with which the sinusoidal deflection proceeds.

In the CT system according to the invention, this course of the intensity curve is determined depending in a value-based manner on the displacement of a grating and measurement of the radiation intensity depending on the grating positions. The phases $x_0$ can then be evaluated for the phase contrast imaging from the knowledge of this curve, or the median values $l_{med}$ and the deflection amplitude $l_{amp}$ can be evaluated in a known manner for a dark field imaging.

Although modifications and changes may be suggested by those skilled in the art, it is the intention of the inventors to embody within the patent warranted hereon all changes and modifications as reasonably and properly come within the scope of their contribution to the art.

We claim as our invention:

1. X-ray CT system for x-ray phase contrast and/or x-ray dark field imaging of a scanned examination subject, comprising:
    at least one grating interferometer arranged at a gantry, said at least one grating interferometer comprising:
        a first grating structure having a plurality of band-shaped x-ray emission maxima and minima arranged in parallel, said maxima and minima exhibiting a first grating period,
        a second band-shaped grating structure that produces, as a phase grating, a partial phase offset of x-ray radiation passing therethrough and that exhibits a second grating period,
        a third band-shaped grating structure with a third grating period with which relative phase shifts of adjacent x-rays and/or scatter components are detected,
        the first, second and third grating structures having respective distances from one another, and at least the respective grating periods of the first and second grating structures satisfying the Talbot conditions, and the third grating structure having a grating period that is larger at least by a factor of 2 to 5 than the grating period of the first grating structure; and
    a device configured for value-based determination of the phase between adjacent x-rays and/or for value-based determination of the spatial intensity curve per detector element perpendicular to the bands of the grating structures.

2. X-ray CT system according to claim 1, wherein the second grating structure has a grating period that is larger by a factor of 1.4 to 2.0 than the grating period of the first grating structure.

3. X-ray CT system according to claim 1 wherein a ratio of the distance between the second grating structure and the third grating structure to the distance between the first grating structure and the second grating structure is in a range l/d=2.5 to l/d=6.

4. X-ray CT system according to claim 1 wherein the grating structures are matched to an x-ray energy in the energy range from 50 keV to 80 keV.

5. X-ray CT system according to claim 1 wherein the at least one grating interferometer has a beam path that, in a direction of a rotation angle of the gantry, exhibits a divergence of at least 30°.

6. X-ray CT system (C1) according to claim 1 wherein the at least one grating interferometer has a beam path that, in a direction of a rotation angle of the gantry, exhibits a divergence of at least 35° to 40°.

7. X-ray CT system according to claim 1 comprising a patient bed that places the examination subject between the second grating structure and the third grating structure.

8. X-ray CT system according to claim 1 wherein a dimension of the first grating structure in a circumferential direction of the gantry is 1 to 3 CM.

9. X-ray CT system according to claim 1 wherein a dimension of the third grating structure in a direction of greatest divergence of radiation striking said grating interferometer is greater by at least a factor of two than a dimension of the second grating structure in said direction of greatest divergence of the radiation.

10. X-ray CT system (C1) according to claim 1 wherein a ratio (l/d) of the distance l between the first and second grating structures and the distance between the second and third grating structures is smaller than 1.

11. X-ray CT system according to claim 10 wherein the ratio (l/d) of the distance l between the first and second grating structures and the distance between the second and third grating structures is between 0.5 and 0.1.

12. X-ray CT system according to claim 1 comprising an x-ray source that emits an x-ray beam from a focus, said x-ray beam propagating in a beam direction, and wherein the first grating structure has a source grating with the focus (F) of the x-ray source situated upstream therefrom in the beam direction.

13. X-ray CT system according to claim 1 comprising an x-ray source having an anode, and wherein the first grating structure is formed by radiation maxima and radiation minima alternatingly emitted in bands at said anode.

14. X-ray CT system according to claim 13 wherein the anode has an inhomogeneously structured anode surface, at which the radiation maxima and radiation minima bands are created.

15. X-ray CT system according to claim 14, wherein the anode surface comprises elevations and/or depressions arranged in bands.

16. X-ray CT system according to claim 14, wherein the anode surface is comprised of materials with different atomic number arranged in bands.

17. X-ray CT system (C1) according to claim 13, wherein said x-ray source comprises an electron emitter that emits an electron beam and a deflection device that electromagnetically deflects the electron beam to scan the anode with the electron beam and to generate the radiation maxima and radiation minima bands.

18. X-ray CT system according to claim 1 wherein the third grating structure comprises at least one analysis grating with a subsequently arranged, spatially resolving detector with a plurality of detector elements.

19. X-ray CT system according to claim 1 wherein the first grating structure comprises a device for monitored spatial offset perpendicular to the gratings thereof and with a spatial resolution approximating the period of the first grating structure.

20. X-ray CT system according to claim 1 wherein the second grating structure comprises a device for monitored spatial offset perpendicular to the gratings thereof, and with a spatial resolution approximating the period of the second grating structure.

21. X-ray CT system according to claim 1 wherein the third grating structure comprises a device for monitored spatial offset perpendicular to the gratings thereof, and with a spatial resolution approximating the period of the second grating structure.

22. X-ray CT system according to claim 1 wherein the third grating structure is formed by a plurality of band-shaped, spatially resolved detector elements per detected x-ray beam.

* * * * *